United States Patent [19]

Marchionni et al.

[11] Patent Number: 4,684,452

[45] Date of Patent: Aug. 4, 1987

[54] PROCESS FOR THE FLUORINATION IN LIQUID PHASE OF UNSATURATED COMPOUNDS

[75] Inventors: Giuseppe Marchionni, Milan; Claudio Tonelli, Concorezzo/Milano; Alberto Nicoletti, Milan, all of Italy

[73] Assignee: Ausimont S.p.A., Milan, Italy

[21] Appl. No.: 847,448

[22] Filed: Apr. 3, 1986

[30] Foreign Application Priority Data

Apr. 4, 1985 [IT] Italy ............................... 20236 A/85

[51] Int. Cl.$^4$ ............................................. B01J 19/12
[52] U.S. Cl. ........................... 204/157.94; 204/157.92; 204/157.95; 204/157.96; 204/157.97; 204/158.1; 204/158.11; 204/158.12

[58] Field of Search ....................... 204/157.92, 157.94, 204/157.95, 157.97, 158.1, 158.12, 157.96

[56] References Cited

U.S. PATENT DOCUMENTS 3,897,502  7/1975  Russell et al. .................. 204/157.94

*Primary Examiner*—Arthur P. Demers
*Attorney, Agent, or Firm*—Stevens, Davis, Miller & Mosher

[57] ABSTRACT

Process for the fluorination with elemental fluorine of fluorinated olefins, carried out in liquid phase using a perfluoropolyether as solvent, at temperatures comprised within the range of from −25° C. to +120° C., by using gaseous fluorine diluted with an inert gas.

4 Claims, No Drawings

PROCESS FOR THE FLUORINATION IN LIQUID PHASE OF UNSATURATED COMPOUNDS

The present invention relates to a new process for the fluorination in liquid phase of unsaturated compounds.

BACKGROUND OF THE INVENTION

Methods are known for fluorinating unsaturated organic compounds by using elemental fluorine. Fluorinating the double bond is a reaction presenting strong difficulties in practical implementation, due to its highly exothermal character, with the evolution of high amounts of heat, of the order of 107 kcal per each double bond. The high reaction energy can lead to strong increases of the reaction mass temperature, within very short times, and hence difficult to control. Locally the temperature can be so high as to cause the breakage of C—C bonds in the product, with the degradation of the same, and the formation of undesired byproducts. Another occurring drawback is the dimerization of the product.

In the processes of the prior art, obviating these drawbacks and dangers has been tried by carrying out the fluorinating reaction under easily controllable conditions: the most common contrivances are the use of very low reaction temperatures, even as low as $-120°$ C., in particular at the beginning of the process, and/or the use of low concentrations of fluorine, which to that purpose is diluted with such inert gases as nitrogen or noble gases (helium).

These contrivances suffer however from some drawbacks: first of all, they extremely reduce the reaction rate, and furthermore, sometimes, the use of low-reactivity conditions does not allow the reaction to be conveniently carried out and consequently, when said reaction, after an initial induction time, starts, the amount of fluorine present in the reaction mixture is higher than its optimum value and can lead to a too fast and uncontrollable reaction.

THE PRESENT INVENTION

According to the process of the present invention, the fluorination is carried out in liquid phase, at a temperature comprised within the range of from $-25°$ C. to $+120°$ C., preferably of from $-10°$ C. to $+70°$ C. in presence of a solvent allowing fluorine concentration to be controlled, and acting as a temperature stabilizer, in such way creating such conditions that fluorine may easily react with no delays; consequently, operating is possible with higher fluorine concentrations, thus increasing the reaction rate.

Essential conditions of the process are:
(1) control of fluorine concentration, carried out by adequately diluting gaseous fluorine with inert gases: mixtures containing from 10% to 80% by volume of fluorine are used;
(2) use of U.V. or visible radiations, to activate the fluorinating reaction: the radiations have wavelength comprised within the range of from 2200 Å to 8000 Å this causes an increase to occur of atomic fluorine concentration, with the consequence that the dimerization of the olefin is prevented, as well as other side reactions;
(3) use of a reaction solvent allowing the temperature to be controlled, transparent to the activating radiations used, of low volatility under the reaction conditions, and constituted by a perfluoroether or perfluoropolyether having a molecular weight not lower than 450 and preferably lower than 2000.

In particular, the products comprised in one of the following structures are suitable:
(I) $R_fO(C_3F_6O)_m(CFXO)_n$—$R_f$ (Fomblin Y) ®, wherein $R_f = CF_3$, $C_2F_5$, $C_3F_7$, X is either F or $CF_3$, m and n are the integers, n can also be 0, and m+n is such as to fulfil the condition that the molecular weight be higher than 450 and preferably lower than 2000, the m and n units being randomly distributed along the chain;
(II) $CF_3O(C_2F_4O)_q$—$CF_3$ (Fomblin Z) ®, wherein p and g are integers, the p/g ratio ranges from 2 to 0.5 and preferably from 1 to 0.5, the monomeric units $C_2F_4O$ and $CF_2O$ are randomly distributed along the chain;
(III) perfluoropolyethers of formula $C_3F_7O(C_3F_6O)_xC_2F_5$ of Krytox ® type, constituted by oligomers of

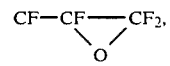

wherein x is an integer;
(IV) $R_f'(CF_2CF_2O)_nR_f'$ wherein n is an integer, and $R_f' = CF_3$, $C_2F_5$;
(V) $A(CF_2CF_2CF_2O)_nB$, wherein n is an integer, $A = F$ or $OR_f'$, $B = R_f'$, or $C_3F_7$. Perfluoropolyethers having one or more of the units indicated above for each class can be also used. Particularly suitable perfluoropolyethers of this type are those containing repeating units:

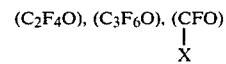

wherein $X = F$, $CF_3$.

These compounds are described for example in U.S. Pat. No. 3,665,041.

Perfluoropolyethers of class (IV) and (V) are described respectively in U.S. Pat. No. 4,523,039 and in published EP appln. 148,482.

The perfluoropolyethers belonging to the above said classes must have an average molecular weight comprised within the range of from 450 to 5000 and preferably of from 500 to 2000.

The process according to the invention is suitable to the fluorinating of perfluorinated linear, cyclic or branched olefins containing from 4 to 12 carbon atoms, with the condition that the branching is not on adjacent atoms, or of perfluoro-vinyl ethers having the general formula

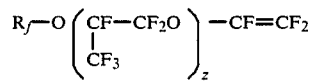

wherein $R_f$ is a perfluorinated radical of from 1 to 3 f carbon atoms, and Z is an integer ranging from 0 to 2, and when $R_f = CF_3$, Z is at least equal to 1, with chains of from 4 to 12 carbon atoms, wherein one or more carbon atoms can be replaced by oxygen atoms.

Examples of linear olefins which can be used are: linear olefins such as $n-C_5F_{10}$, $n-C_7F_{14}$; branched olefins such as

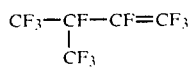

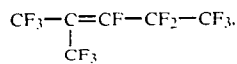

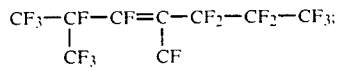

cyclic olefins such as:

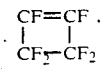

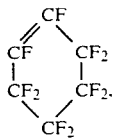

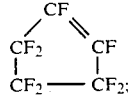

Examples of perfluorovinylethers which can be used
$CF_3CF_2CF_2-O-CF=CF_2$,

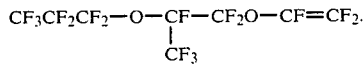

The following Examples are given to illustrative purposes and are not to be intended as being limitative of the possibilities of practical embodiment of the present invention.

EXAMPLE 1

The fluorination tests are carried out within a cylindrical photochemical reactor of 250 cc of capacity, provided with a quartz coaxial sheath for housing a 150-W mercury-vapour lamp type Hanau TQ 150, moreover provided with a bubbling gas inlet, magnetic stirrer, $CCl_3/CO_2$ trap, and with a temperature control system both for the reactor and for the sheath system, using perfluorinated liquids (type FC-75).

Into the photochemical reactor described above, 150 g of perfluoro-2-methylpentene-3 with minor amounts of perfluoro-2-methylpentene-2, obtained by dimerization, catalyzed by anhydrous KF, of perfluoropropene in acetonitrile, together with 150 g of solvent, constituted by a perfluoropolyether of type (I), obtained from perfluoropropene, and having viscosity $\eta=8$ cSt (at 20° C.), are charged.

Subsequently, after the turning on of the lamp, the system is kept at the constant temperature of $-20°$ C., and the fluorination is carried out with a fluorine stream of 2.5 l/h, diluted with a 7.5 l/h nitrogen stream.

During 10 hours, the flow rate of fluorine is progressively increased up to 5 l/h, and the nitrogen flow rate is reduced to 3 l/h.

At the end of the reaction, before drawing the product, the fluorine present is removed by means of a nitrogen stream; the reaction product is submitted to rectification, and as low-boiling products, 2.5 g of unreacted olefin and 16.7 g of 99% perfluoroisohexane (perfluoro-2-methyl-pentane) having boiling point 57° C. and formula:

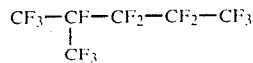

are obtained.

The residue is the perfluoropolyether used as solvent.

EXAMPLE 2

Into the same equipment as of Example 1, 60 g of perfluoro-2-methylpentene-3 with minor amounts of perfluoro-2-methylpentene-2 and 240 g of solvent constituted by perfluoropolyether of type (I), obtained from perfluoropropene, with viscosity $\eta=8$ cSt (at 20° C.) are charged. Subsequently, after the turning on of the lamp, the system is kept at the constant temperature of $-20°$ C., and the fluorination is carried out with a fluorine stream of 2.5 l/h, diluted with a 7.5 l/h nitrogen stream.

During 5 hours, the flow rate of fluorine is progressively increased up to 5 l/h, and the nitrogen flow rate is reduced to 5 l/h; during the same time, the temperature is increased from $-20°$ C. to 0° C.

At the end of the reaction, after the removal of fluorine, the reaction product is submitted to rectification, and 64.2 g of perfluoro-2-methylpentane (yield 95%) are obtained.

We claim:

1. Process for the fluorination with elemental fluorine of perfluorinated olefins containing from 4 to 12 carbon atoms, linear, cyclic or branched, with the condition that the branching is not on adjacent atoms, or of perfluoro-vinyl ethers having the general formula

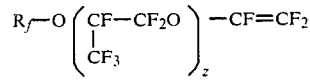

wherein $R_f$ is a perfluorinated radical of from 1 to 3 carbon atoms, and z is an integer ranging from 0 to 2, and when $R_f=CF_3$, z is at least equal to 1, with chains containing from 4 to 12 carbon atoms, wherein one or more carbon atoms can be replaced by oxygen atoms, the fluorination being carried out in liquid phase comprising as the reaction solvent a low-volatility perfluoroether, having molecular weight not lower than 450, the reaction being carried out at a temperature comprised within the range of from $-25°$ C. to $+120°$ C., in the presence of activating radiations comprised within the visible spectrum on in U.V. range, having wavelength comprised within 2200 Å and 8000 Å, and with the use of gaseous mixtures of fluorine and inert gas, containing from 10% to 80% by volume of fluorine.

2. Process according to claim 1, furthermore characterized in that the perfluoroether used as the reaction solvent is selected from the products comprised in the following general formulae:

(I) 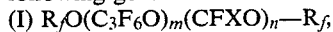

wherein $R_f=CF_3$, $C_2F_5$, $C_3F_7$, X is either F or $CF_3$, m nd n are intergers, n can also be O, and m+n is such as to fulfil the condition that the molecular weight be higher than 450 and preferably lower than 2000, the m and n units being randomly distributed along the chain, (II) $CF_3O(C_2F_4O)_p(CF_2O)_q-CF_3$ wherein p and g are integers, the p/g ratio ranges from 2 to 0.5 and preferably from 1 to 0.5, the monomeric units $C_2F_4O$ and $CF_2O$ are randomly distributed along the chain, (III) perfluoropolyethers of formula $C_3F_7O(C_3F_6O)_xC_2F_5$,

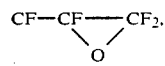

wherein x is an integer.

3. Process according to claim 1, furthermore characterized in that the perfluoroether used as the reaction solvent is selected from the products comprised in the following general formulae:

(IV) $R_f'(CF_2CF_2O)_nR_f'$ wherein n is an integer, and $R_f'=CF_3, C_2F_5$;

(V) $A(CF_2CF_2CF_2O)_nB$ wherein n is an integer, $A=F$ or $OR_f'$, $B=R_f'$ or $C_3F_7$.

(VI) perfluoropolyethers containing repeating units:

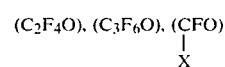

wherein $X=F, CF_3$.

4. Process according to claims from 1 to 3, furthermore characterized in that fluorine is diluted with nitrogen.

* * * * *